US00PP19062P3

(12) United States Plant Patent
Olesen

(10) Patent No.: US PP19,062 P3
(45) Date of Patent: Aug. 5, 2008

(54) MINIATURE ROSE PLANT NAMED 'POULPAR039'

(50) Latin Name: *Rosa* hybrid
Varietal Denomination: Poulpar039

(75) Inventor: Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 290 days.

(21) Appl. No.: 11/360,914

(22) Filed: Feb. 22, 2006

(65) Prior Publication Data

US 2007/0199110 P1 Aug. 23, 2007

(51) Int. Cl.
*A01H 5/00* (2006.01)

(52) U.S. Cl. ..... Plt./116

(58) Field of Classification Search ..... Plt./116
See application file for complete search history.

*Primary Examiner*—Annette H Para

(57) ABSTRACT

A new miniature rose plant that has abundant, pink and apricot blended flower petals and attractive foliage. The variety successfully propagates from softwood cuttings and is suitable for year-round production in commercial glasshouses. This new and distinct variety has shown to be uniform and stable in the resulting generations from asexual propagation.

1 Drawing Sheet

Botanical designation: *Rosa* hybrid.
Variety denomination: 'Poulpar039'.

SUMMARY OF THE INVENTION

The present invention constitutes a new and distinct variety of miniature rose plant which originated from a controlled crossing between the female seed parent 'Poulhi008', U.S. Plant Pat. No. 15,722, and the male pollen parent, an unnamed seedling.

The two parents were crossed during the summer of 2002 and the resulting seeds were planted in a controlled environment in Fredensborg, Denmark. The new variety, named 'Poulpar039', originated as a single seedling from the stated cross.

The new variety may be distinguished from its female seed parent primarily by flower color. The seed parent variety has flowers which are generally Red Group 55B in color. 'Poulpar039' has a general flower color of Red Group 56C to Red-Purple Group 62D with intonations of Red Group 49A.

The new variety may be distinguished from its male pollen parent primarily by flower color. The pollen parent variety has a general flower color of Yellow 12 C. 'Poulpar039' has a general flower color of Red Group 56C to Red-Purple Group 62D with intonations of Red Group 49A.

The objective of the hybridization of this rose variety for commercial culture was to create a new and distinct variety with unique qualities, such as:

1. Uniform and abundant pink apricot blend flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type, known to the inventors, and distinguish 'Poulpar039' from all other varieties of which we are aware.

As part of the rose development program, Mogens N. Olesen germinated the seeds from the aforementioned hybridization and conducted evaluations on the resulting seedlings in a controlled environment in Fredensborg, Denmark. 'Poulpar039' was selected by the inventor as a single plant from the progeny of the hybridization in 2003.

Asexual reproduction of 'Poulpar039' by cuttings and traditional budding was first done by Mogens N. Olesen in the nursery in Fredensborg, Denmark in April 2003. This initial and other subsequent propagations conducted in controlled environments have demonstrated that the characteristics of 'Poulpar039' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'Poulpar039'. Specifically illustrated in the drawing:

FIG. 1.1; Cluster of unopened flower buds;

FIG. 1.2; Views of open flower and flower petals, detached;

FIG. 1.3; Flower reproductive parts and sepals, detached;

FIG. 1.4; Mature and juvenile leaves; and

FIG. 1.5; Bare stem.

DETAILED DESCRIPTION OF THE VARIETY

The following is a description of 'Poulpar039', as observed in its growth in a glasshouse located in Fredensborg, Denmark Observed plants are 3 months of age and were cultivated in 10.5 cm pots. Color references are made using The Royal Horticultural Society (London, England) Colour Chart, 2001, except where common terms of color are used.

For a comparison, several physical characteristics of the rose variety 'Poulpar030', U.S. Plant Pat. No. 16,855, are compared to 'Poulpar039' in Chart 1.

CHART 1

| Characteristic | 'Poulpar039' | 'Poulpar030' |
|---|---|---|
| Upper surface of petals upon opening | Red Purple Group 62D with intonations of Orange Group 26C at the middle zone | Yellow-Orange Group 14C |
| Petal Count | 40 | 25 |

FLOWER AND FLOWER BUD

Blooming habit: Continuous.

Flower bud:

*Size.*—Upon opening, 22 mm in length from base of receptacle to end of bud. Bud diameter is 11 mm.

*Bud form.*—Pointed ovate.

*Bud color.*—As sepals unfold, petals are Red Group 37B.

*Sepals.*—Upper Surface: Color: Green Group 138B. Texture: Smooth and moderately pubescent. Lower Surface: Color: Yellow Green Group 144A. Texture: Smooth with few stipitate glands and light pubescence. Shape: Apex: Cirrhose. Base: Flat at union with receptacle. Margins: Margins have weak foliaceous appendages on three of the five sepals. Size: 25 mm long by 6 mm wide.

*Receptacle.*—Surface Texture: Smooth. Shape: Urn-shaped. Size: 7 mm (h)×6 mm (w). Color: Yellow Green Group 144A. Anthocyanin: None observed.

*Pedicel.*—Surface: Smooth and lightly pubescent. Length: 20 mm average length. Diameter: 3 mm. Color: Yellow-Green Group 144B. Strength: Medium strength.

*Borne.*—Singly or in small clusters of 3 buds per flowering stem.

Flower bloom:

*Fragrance.*—Medium rose scent.

*Duration.*—As a pot plant, flowers last up to 28 days. Petals fall cleanly away from plant after flowers have fully matured.

*Size.*—Normally 60 mm in diameter 23 mm in height.

*Form.*—General shape is a rosette with many slightly overlapping petals of different sizes.

*Shape of flower, side view.*—Upon opening: The upper portion is flat. The lower portion is flattened convex. After opening: The upper portion is flat. The lower is flattened convex.

Petalage: There are normally 40 petals, 3 to 7 of which are petaloids.

Color:

*Upon opening, petals.*—Outermost petals: Upper Surface: Red-Purple Group 62D with intonations of Orange Group 26C at the middle zone. Lower Surface: Red-Purple Group 62D at the margins with Red-Purple Group 62C at the middle zones. Innermost petals: Upper Surface: Orange Group 27A to Red Group 56D. Lower Surface: Red Group 38B. Basal petal spots upon opening: Upper surface: Yellow Group 8C. Lower surface: Green-Yellow Group 1D.

*After opening, petals.*—Outermost petals: Upper Surface: Red-Purple 62D. Lower Surface: Red Group 56A to Red-Purple Group 62C. Innermost petals: Upper Surface: Red-Purple 62D. Lower Surface: Red Group 56A to Red-Purple Group 62C.

*After opening, basal petal spots.*—Upper surface: Yellow Group 11C to 11D. Lower surface: Yellow Group 11D.

General tonality: On open flower Red Group 56C to Red-Purple Group 62D with intonations of Red Group 49A.

Petals:

*Petal reflex.*—Medium petal reflex at margins.

*Petal margin.*—Entire with point at the center.

*Shape.*—Generally broad elliptical. Base: Obtuse. Apex: Cuspidate.

*Size.*—Petal size varies. Outer petals are 30 mm (l)×30 mm (w). Inner petals are 20 mm (l)×20 mm (w).

*Texture.*—Smooth.

*Thickness.*—Average to somewhat thin.

Petaloids:

*Quantity.*—On average there are 3 to 7.

*Size.*—22 mm long×10 mm wide.

*Shape.*—Apex is round with generally elliptical and irregular. Base is acute.

*Color.*—Upper Surface: Red Group 62D. Lower Surface: Red Group 56A to Red-Purple Group 62C.

Reproductive organs:

*Pollen.*—None observed.

*Anthers.*—Size: 2 mm long. Color: Yellow Group 4D. Quantity: 65 to 70.

*Filaments.*—Color: Yellow Group 8C. Length: Normally 6 mm.

*Pistils.*—Length: Normally 4 mm long. Quantity: 25 to 30.

*Stigmas.*—Superior in relative to the length of the filaments and the height of the anthers. Color: Greyed-Yellow Group 162D.

*Styles.*—Color: Red Group 46B.

*Seed formation.*—Not observed.

PLANT

Plant growth: Moderate upright to bushy. Very compact. When grown as an 8–11 cm pot plant on its own roots, the average height of the plant itself is 15 to 17 cm and the average width is 15 cm.

Stems:

*Color.*—Young wood: Yellow-Green Group 146B. Older wood: Yellow-Green Group 146A.

*Internodal distance.*—On mature canes, 20 mm.

*Length of stems.*—On average, canes are 10 cm from the base of the stem to the flowering portion.

*Diameter.*—2 to 2.5 mm.

*Surface texture.*—Young wood: Smooth. Older wood: Somewhat rough with small prickles.

Prickles: None observed.

Plant foliage: Normal number of leaflets on normal leaves in middle of the stem: 5 to 7 leaflets.

*Compound leaf size.*—68 to 81 mm (l)×45 to 50 mm (w).

*Quantity.*—5 leaves per 10 cm of stem.

*Color.*—Juvenile foliage: Upper Leaf Surface: Yellow-Green Group 146A. Lower Leaf Surface: Yellow-Green Group 146B. Anthocyanic intonations of Greyed-Red Group 183A on the upper margins. Mature foliage: Upper Leaf Surface: Yellow-Green Group 147A. Lower Leaf Surface: Yellow-Green Group 148C to Greyed-Green Group 194A.

Plant leaves and leaflets:

*Stipules.*—Size: 6 to 7 mm in length. Shape: Linear, slightly broad based with outward extending apecies.

Margins: Finely serrated with many stipitate glands. Color: Green Group 138A.

*Petiole.*—Length: 18 mm. Upper surface: Color: Yellow-Green Group 146B with anthocyanic pigments of Greyed-Red Group 181A. Observations: Few stipitate glands. Lower surface: Color: Yellow-Green Group 146C. Observations: Few small prickles observed.

*Rachis.*—Size: 20 to 25 mm in length. Upper surface: Color: Yellow-Green Group 146B with anthocyanic pigments of Greyed-Red Group 181A. Observations: Few stipitate glands. Lower surface: Color: Yellow-Green Group 146C. Observations: Few small prickles observed.

Leaflet: Size: Normally 30 to 37 mm in length by 17 to 20 mm wide. Edge: Serrated. General Shape: Ovate. Apex Shape: Acute. Base Shape: Obtuse. Texture: Smooth. Thickness: Average. Arrangement: Odd pinnate. Venation: Reticulate. Leaf Gloss: Matte finish.

Disease resistance: Average resistance to powdery and downy mildew, black spot, and *Botrytis* under normal growing conditions in Fredensborg, Denmark.

It is claimed:

1. A new and distinct variety of rose plant of the miniature class named 'Poulpar039', substantially as illustrated and described herein, due to its abundant, pink and apricot blended flower petals, vigorous growth, compact habit, suitability for production from softwood cuttings in pots, and durable flowers and foliage that make the variety suitable for distribution in the floral industry.

* * * * *

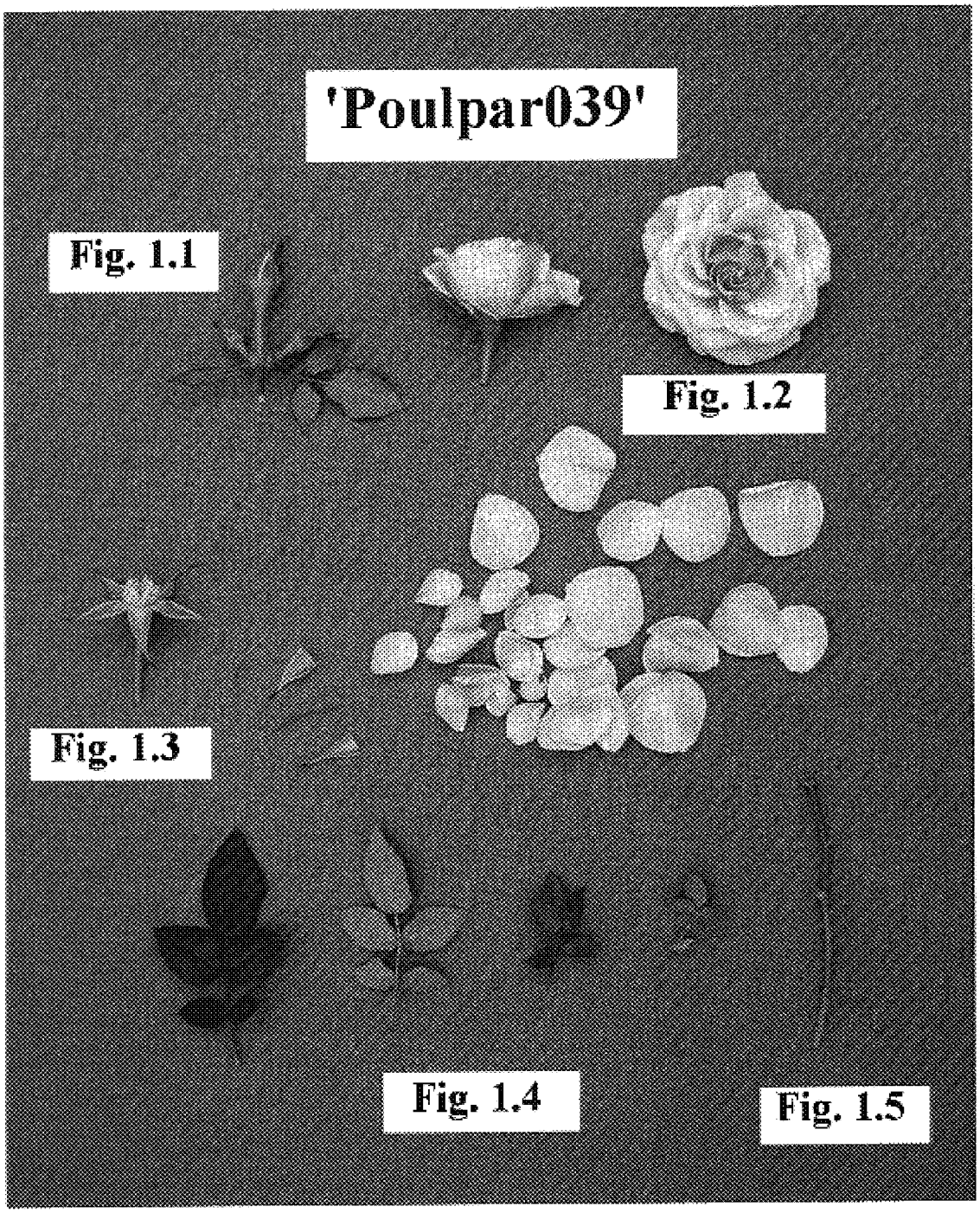
'Poulpar039'
Fig. 1.1
Fig. 1.2
Fig. 1.3
Fig. 1.4
Fig. 1.5